United States Patent
Tan et al.

(10) Patent No.: US 9,386,762 B2
(45) Date of Patent: Jul. 12, 2016

(54) CELL LINE OF RENAL SARCOMATOID CARCINOMA IN PERSONS OF HAN NATIONALITY AND PREPARATION METHOD THEREOF

(75) Inventors: Xiaojie Tan, Shanghai (CN); Yifang Han, Shanghai (CN); Wei Guan, Shanghai (CN); Wenjun Chang, Shanghai (CN); Guangwen Cao, Shanghai (CN)

(73) Assignee: SECOND MILITARY MEDICAL UNIVERSITY (CN)

( * ) Notice: Subject to any disclaimer, the term of this patent is extended or adjusted under 35 U.S.C. 154(b) by 39 days.

(21) Appl. No.: 14/233,087

(22) PCT Filed: Jul. 19, 2012

(86) PCT No.: PCT/CN2012/078874
§ 371 (c)(1),
(2), (4) Date: Jan. 15, 2014

(87) PCT Pub. No.: WO2013/010493
PCT Pub. Date: Jan. 24, 2013

(65) Prior Publication Data
US 2015/0135342 A1     May 14, 2015

(51) Int. Cl.
| | | |
|---|---|---|
| *A01K 67/027* | (2006.01) | |
| *C12N 5/07* | (2010.01) | |
| *C12N 5/09* | (2010.01) | |
| *C12N 5/071* | (2010.01) | |

(52) U.S. Cl.
CPC .......... *A01K 67/0271* (2013.01); *C12N 5/0686* (2013.01); *C12N 5/0693* (2013.01); *A01K 2227/105* (2013.01); *A01K 2267/0331* (2013.01)

(58) Field of Classification Search
None
See application file for complete search history.

(56) References Cited

FOREIGN PATENT DOCUMENTS

| CN | 101508972 A | 8/2009 |
|---|---|---|
| CN | 101550407 A | 10/2009 |
| CN | 102286429 A | 12/2011 |

OTHER PUBLICATIONS

Pradham et al, Dianostic PAthology, 20009, vol. 4, ages 1-8.*
Guangzhi, et al., "Establishment and Characterization of Human Ovarian Sarcomatoid Carcinoma Cell Line BUPH: OVSC-1," Chinese J Clinical Oncology, vol. 31, No. 1, pp. 19-28 (Dec. 31, 2004).
Guangzhi, et al., "The Biological Characteristics of Immortalized Human Ovarian Sarcomatoid Carcinoma Cells and Their Chemosensitivity," Chin J Clin Obst Gynecol, vol. 7, No. 5, pp. 355-357 (Sep. 30, 2006).
International Search Report and Written Opinion issued by the State Intellectual Property Office of the People's Republic of China for International Application No. PCT/CN2012/078874 mailed Nov. 8, 2012 (15 pgs.).
Xiquan, T. and Nianzeng, Xing, "Renal Sarcomatoid Carcinoma and Carcinosarcoma," Journal of Clinical Urology, vol. 23, No. 8, pp. 584-586 (Aug. 31, 2008).
Kim, et al., "Using Percentage of Sarcomatoid Differentiation as a Prognostic Factor in Renal Cell Carcinoma," Clin Genitourinary Cancer, vol. 13, Issue 3, pp. 225-230 (Jun. 2015).
Pal, et al., "RNA-seq Reveals Aurora Kinase-driven mTOR Pathway Activation in Patients with Sarcomatoid Metastatic Renal Cell Carcinoma," Mol Cancer Res., vol. 13(1), pp. 130-137 (Jan. 2015).
Shuch, et al., "Sarcomatoid Renal Cell Carcinoma: A Comprehensive Review of the Biology and Current Treatment Strategies," The Oncologist, vol. 17, pp. 46-54 (2012).
Zhang, et al., "A Novel Prognostic Model for Patients with Sarcomatoid Renal Cell Carcinoma," BJU Int., vol. 115, Issue 3, pp. 405-411 (Mar. 2015).

* cited by examiner

*Primary Examiner* — Karen Canella
(74) *Attorney, Agent, or Firm* — Wilmer Cutler Pickering Hale and Dorr LLP

(57) ABSTRACT

Provided is a renal sarcomatoid cell line RCC09HYF, of which the deposit No. is CCTCC C201130, and the preparation method of the renal sarcomatoid cell line. The renal sarcomatoid cell line RCC09HYF can grow for a long period and be steadily passaged in vitro. By tumorigenic experiments using in-situ animal models in vitro it has been found that: the tumorigenesis is relatively fast inside animals and 3-4 weeks after tumor inoculation, the transplanted tumors fill the whole abdominal cavity, and dyscrasia appears in above 50% of nude mice; moreover, lung metastasis is present in a few individuals. The renal sarcomatoid cell line RCC09HYF can provide an effective and steady cell model for further study of the genesis and metastasis mechanism of renal sarcomatoid carcinoma in persons of Han nationality and for clinical prediction, diagnosis and treatment.

12 Claims, 4 Drawing Sheets

A　　　　　　　　　　B

CAM

Vimentin

CD10

Ki67

CELL LINE OF RENAL SARCOMATOID CARCINOMA IN PERSONS OF HAN NATIONALITY AND PREPARATION METHOD THEREOF

The present application is a National Phase under 35 U.S.C. 371 of PCT/CN2012/078874, which claims priority to Chinese application No. 201110202556.5, filed to The Patent Office of the People's Republic of China on Jul. 20, 2011, titled "Cell line of renal sarcomatoid carcinoma in persons of Han nationality and preparation method thereof", the entire contents of both are hereby incorporated by reference.

FIELD OF INVENTION

The present invention relates to the field of microbiological and animal cell line, particularly, to the cell line of sarcomatoid renal cell carcinoma (RCC) in Han Chinese (RCC09HYF) and the generation method thereof.

BACKGROUND OF THE INVENTION

Cell line is of great importance for basic research of cancer. In vitro experiments using cell lines and subsequent construction of animal models are the essential approaches to find out the potential functions of important genes in the postgenomic era, especially for the functional genomics era. At present, cell lines are still extensively used as an important tool for characterizing gene functions in vitro, due to their relatively steady genetic background. Tumor cell lines are of great importance not only for deeply exploring the mechanisms of tumorigenesis and progression at molecular or genetic level, but also for early diagnosis, medicine screening and cancer therapy. For example, treatment of metastatic clear cell RCC using sunitinib malate is now at phase III clinical trial, based on the in vitro function of this medicine on RCC cell lines such as 786-O.

Sarcomatoid RCC (sRCC) is a specific RCC entity, which accounts for only 1.0-8.0% of renal cell tumors and there are rare sRCC cases in clinic. sRCC presents highly aggressive malignancy, and progressions of sRCC patients go rapidly, usually with early metastasis. sRCC patients are not sensitivity to chemotherapy or radiotherapy and have extremely poor prognosis. The average survival time of T1 patients is 49.7 months, while it is 6.8 months for T2~T4 patients. In 1968, Farrow and his colleagues firstly discovered and named sarcomatoid RCC (Farrow G M, Harrison E G, UTZ DG. Sarcomas and sarcomatoid and mixed malignant tumor s of the kidney in adults-Part III. Cancer 1968, 22: 556-563). For the components of this type of tumor, the epithelial component can be a renal cell carcinoma of various pathological types, 70% of which is clear cell or chromophobe granule type; while the sarcomatoid component can be hemangiopericytosarcomatoid, rhabdomyosarcomatoid, osteosarcomatoid, chondrosarcomatoid and undifferentiated sarcomatoid structure, et al. At present, early diagnosis with subsequent radical nephrectomy is preferred alternative of sRCC patients, since there is no breakthrough in diagnosis and treatment of sRCC. A few sRCC cases have been reported to be sensitive to cytokine therapy, which are only case reports and have not been verified by randomized control trials. Furthermore, prognosis and therapeutic effect are directly influenced by the proportion between the sarcomatoid and epithelia components in sRCC, in which the higher proportion the sarcomatoid component accounts for, the poorer the prognosis is, and the harder the systematic treatment will be. In order to elucidate the genetic properties of sRCC, particularly the effect of the interaction between the sarcomatoid and epithelia components on RCC malignancy, thereby guiding systematic treatment, it is required and necessary to establish sRCC cell lines.

At present, ATCC has not deposited any sRCC cell lines. Since the genetic background and living conditions varied among races all over the world, tumor morbidity and fatality rates are also different. Thus, it is the essential step and of great scientific value to establish the cell line of sRCC derived from Han Chinese, which contributed to exploring the mechanism of RCC metastasis.

SUMMARY

An objective of the present invention is to provide a sRCC cell line from Han Chinese.

In the present invention, a human cell line of sRCC was established by in vitro cell culture. Taken sRCC cell line to study tumor cell biology including growth and metastasis, et al, it will help to better understand the mechanisms of RCC initiation and metastasis, and contributed to clinic prediction, diagnosis and treatment of RCC in Han Chinese.

In the present invention, the sRCC cell line (named RCC09HYF) of a Han Chinese deposited as No. CCTCCC201130 in China Center for Type Culture Collection, Wuhan University, Wuhan 430072, China on May 11, 2011 is provided.

In the present invention, also provided is a method for generation of the above-mentioned sRCC cell line from a Han Chinese (RCC09HYF) comprising the following steps:

RCC09HYF cell line of the present invention originated from the primary tumor tissues of the Han Chinese sRCC patient. The resected tumor tissue is placed into a petri-dish supplied with a little serum-free DMEM medium (containing 1000 U/ml penicillin and 3 µg/ml amphotericin B). After necrotic tissue, adipose connective tissue and blood vessels are removed, the visible tumor tissue identified by naked eyes is immersed in serum-free DMEM medium at 4° C. for 30 min and then cut into 1~3 mm$^3$ pieces with an ophthalmic scissor. The tissue pieces are transferred into centrifuge tube together with the medium, and washed by shaking for 2~3 min and centrifuged at 1500 rpm for 10 min. The supernatant is discarded, and the tissue pieces are resuspended by adding DMEM medium, and washed by shaking for 2~3 min and centrifuged at 1500 rpm for 10 min. The supernatant is discarded, and the tissue pieces are suspended in 1 ml DMEM complete medium (DMEM medium, 10% fetal bovine serum, 100 U/ml penicillin, and 100 µg/ml streptomycin), and seeded into glass cell culture flask (100 ml). The flask is kept in a $CO_2$ incubator for 24 h at 37° C. under 5% $CO_2$ and 95% humidity. After 24 h, the adherent tissue pieces are supplemented with 2~2.5 ml DMEM complete medium to keep incubation.

A method in detail for generating sRCC cell line from a Han Chinese (RCC09HYF) of the present invention is as follows:

1. Primary Cell Culture

Primary renal tumor tissue (pathologically identified as sarcomatoid renal cell carcinoma afterwards) is obtained from a patient received radical nephrectomy under aseptic condition. The tumor tissues are kept in a little serum-free DMEM medium (containing 1000 U/ml penicillin and 3 µg/ml amphotericin B) in a petri-dish. After necrotic tissue, adipose connective tissue and blood vessels are removed, the visible tumor tissues identified by naked eyes are immersed in serum-free DMEM medium at 4° C. for 30 min and then cut into 1~3 mm$^3$ pieces with an ophthalmic scissor. The tissue pieces are transferred into centrifuge tube with the immersing medium, and washed by shaking for 2~3 min and centrifuged at 1500 rpm for 10 min. The supernatant is discarded, and the tissue pieces are resuspended by adding DMEM medium, and washed by shaking for 2~3 min and centrifuged at 1500 rpm for 10 min. The supernatant is discarded. The tissue pieces are suspended in 1 ml DMEM complete medium, and seeded into glass cell culture flask (100 ml). The flask is kept in a $CO_2$ incubator for 24 h at 37° C. under 5% $CO_2$ and 95% humidity. After 24 h, adherent tissue pieces are supplemented with 2~2.5 ml DMEM complete medium for further incubation.

2. Passage

When cells grow out of the tissue pieces and reaches to 85% confluence, they are passaged. Under aseptic condition in a clean bench, the medium is removed and cells are washed twice with D-hanks solution. And then 1 ml 0.25% trypsin is added, and the flask is placed in a $CO_2$ incubator at 37° C. under 5% $CO_2$ and 95% humidity for 4~5 min. When cytoplasmic retraction and increased intercellular space of most cells are observed under microscope (even a few floating cells are observed), 4 ml DMEM complete medium is added for neutralization. Cells are resuspended to single cells by pipetting.

3. Cryopreservation and Recovery

Cryopreservation: DMEM complete medium is refreshed 24 h before cryopreservation, so as to keep cell growth in logarithmic phase. The medium is removed from the flask under aseptic condition in a clean bench. After adherent cells are washed twice with D-hanks solution, 1 ml 0.25% trypsin is added and the flask is kept in a $CO_2$ incubator at 37° C. under 5% $CO_2$ and 95% humidity for 4~5 min. When cytoplasmic retraction and increased intercellular space of most cells are observed under microscope (even a few floating cells are observed), 4 ml DMEM complete medium is added. Single cell suspension is obtained by pipetting and cell pellet is collected by centrifuge at 1500 rpm for 10 min at room temperature. And then the cells are resuspended with 1.5 ml cryopreservation solution and cell counting is performed so as to adjust the concentration of cells to $5 \times 10^6$ cells/ml. Cell suspension is transferred into a cell freezing tube and sealed carefully. The freezing tube is labeled with the following information: cell type, date of cryopreservation and name of the operator. The cryopreservation tube is placed at −80° C. for over 12 h, and kept in liquid nitrogen on the next day.

Recovery: Cell freezing tube is taken out of liquid nitrogen and immersed in warm water at 37° C. rapidly. After cell suspension is thawed, it is transferred into a centrifuge tube and centrifuged at 1500 rpm for 10 min. The supernatant is discarded. A total volume of 5 ml DMEM complete medium is added to suspend the pellet to single cell suspension with the concentration of $5 \times 10^5$ cells/ml by pipetting. Then the suspension is transferred to a culture flask and incubated in a $CO_2$ incubator at 37° C. under 5% $CO_2$ and 95% humidity.

At present, RCC09HYF cells of No. 64 and 69 passages cultured by us are deposited at China Center for Type Culture Collection.

The formulations of the culture solutions of the present invention are as follows:

D-Hanks solution: NaCl 8.0 g, KCl 0.4 g, $Na_2HPO_4$ $12H_2O$ 0.08 g, $KH_2PO_4$ 0.06 g, $NaHCO_3$ 0.35 g, 1% phenol-red 2 ml are dissolved in ultra-pure water to the volume of 1000 ml. The solution is autoclaved at 121° C. for 30 min, and stored at 4° C.

DMEM medium: Hyclone, Invitrogen (high glucose, supplemented with sodium pyruvate and L-glutamine).

DMEM complete medium: DMEM medium, 10% fetal bovine serum, penicillin 100 U/ml, streptomycin 100 m/ml.

Cryopreservation solution (freshly prepared before use): The cryopreservation solution is composed of fetal bovine serum and dimethyl sulfoxide (DMSO) with a volume ratio of 14 to 20:1.

RCC09HYF, the sRCC cell line from Han Chinese of the present invention, is able to grow in vitro and be stably passaged for a long period of time. The cell line has the characteristics of diphasic differentiation and is composed of the sarcomatoid and epithelial components (the main part is clear cell type), with lack contact of inhibition. The chromosomes of RCC09HYF were heteroploidy, with the number of chromosomes mainly ranged from 55 to 68 and the modal number of 63. The aberrations of both chromosome number and structure exists. After 120 passages for 12 months, the doubling time is 18 h with a colony formation rate of 31% Immunohistochemical analysis for the original tumor tissue of RCC09HYF shows positive expression of Vimentin, CD10, CAM and Ki67, and negative expressions of ABC, CACP, HMB, P53 and SMA.

For RCC09HYF, the sRCC cell line from Han Chinese of the present invention, its tumorigenesis is relatively stronger by in vitro orthotopic animal model. Three to four weeks after transplantation of RCC09HYF cells into nude mice, the whole abdominal cavity is full of tumor in above 50% of nude mice and dyscrasia appears; moreover, lung metastasis is detected in the individual mice. The recovery rate of tumor cells originated from transplant tumor after cryopreservation is more than 80%, and growth status and cell morphology are similar as the original ones.

Taking RCC09HYF, the sRCC cell line from Han Chinese of the present invention, as the experimental tool, growth feature of tumor cells and related malignant biological behavior, including invasion and metastasis, et al, can be characterized. Thus it provides an effective and steady cell model for further studies on renal carcinogenesis and metastasis, and for the clinic prediction, diagnosis and treatment of the sRCC.

The establishment of the sRCC cell line from Han Chinese of the present invention (RCC09HYF) contributed to screening specific markers and therapeutic targets for early detection and effective treatment of sRCC.

DESCRIPTION OF THE PREFERRED EMBODIMENTS

Figure 1:
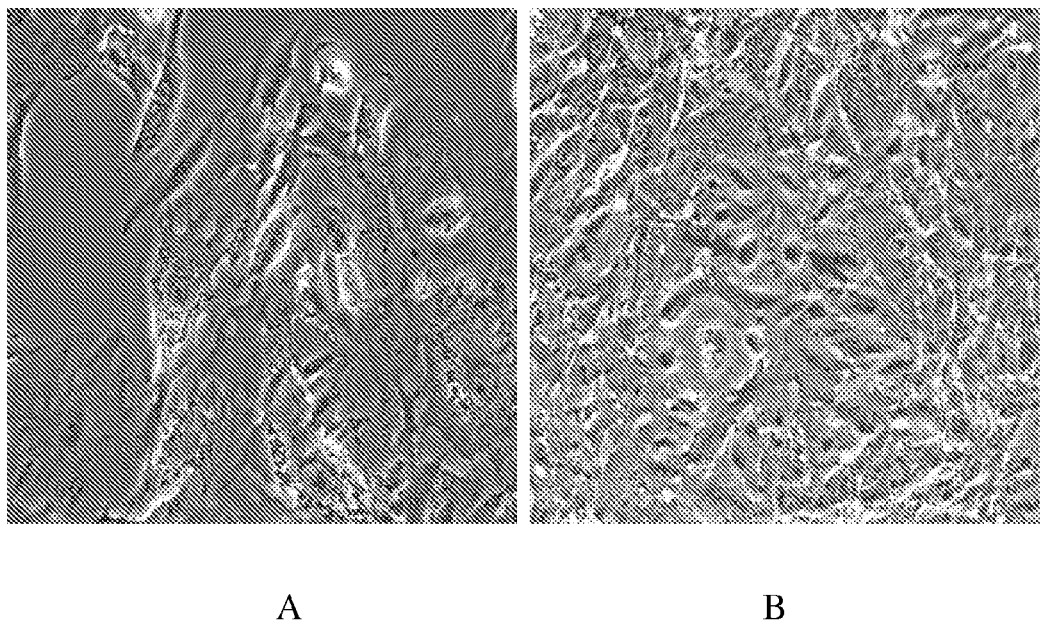
FIG. 1 shows the morphology of RCC09HYF cells of passage 12 under an optical microscope (200×): all the cells were adherent; at the early stage of culture, the cellular shape was extremely irregular with lack contact of inhibition, and the cells exhibited diphasic differentiation (A) and high heterogeneity (B). Some cells showed sarcomatoid structure (denoted by blue arrow), while others showed epithelial structure-clear cell carcinoma (denoted by red arrow).

The present invention will be further explained below with reference to the Examples and Figures of the present invention. The following Examples are performed based on the embodiments of the present invention. Although detailed embodiments and specific operating procedures are provided, the protection scope of the present invention is not limited to the following examples.

Example 1

Preparation of the Cell Line of Human sRCC from a Han Chinese (RCC09HYF)

1. Primary Culture:

Primary renal tumor tissue (pathologically identified as sarcomatoid renal cell carcinoma afterwards) was obtained from a patient received radical nephrectomy under aseptic condition. The tumor tissue was kept in a little serum-free DMEM medium (containing 1000 U/ml penicillin and 3 µg/ml amphotericin B) in a petri-dish. After necrotic tissue, adipose connective tissue and blood vessels were removed, the visible tumor tissues identified by naked eyes were immersed in serum-free DMEM medium at 4° C. for 30 min and then cut into 1~3 mm³ pieces with an ophthalmic scissor. The tissue pieces were transferred into centrifuge tube with the immersing medium, and washed by shaking for 2~3 min and centrifuged at 1500 rpm for 10 min. The supernatant was discarded, and the tissue pieces were resuspended by adding DMEM medium, and washed by shaking for 2~3 min and centrifuged at 1500 rpm for 10 min. The supernatant was discarded. The tissue pieces were resuspended in 1 ml DMEM complete medium, and seeded into glass cell culture flask (100 ml). The flask was incubated in a $CO_2$ incubator for 24 h at 37° C. under 5% $CO_2$ and 95% humidity. After 24 h, adherent tissue pieces were supplemented with 2~2.5 ml DMEM complete medium for further incubation.

2. Passage:

When cells grew out of the tissue pieces and reached to 85% confluence, they were passaged. Under aseptic condition in a clean bench, the medium was removed and cells were washed twice with D-hanks solution. And then 1 ml 0.25% trypsin was added, and the flask was placed in a $CO_2$ incubator at 37° C. under 5% $CO_2$ and 95% humidity for 4-5 min. When cytoplasmic retraction and increased intercellular space of most cells were observed under microscope (even a few floating cells were observed), 4 ml DMEM complete medium was added for neutralization. Cells were resuspended to single cells by pipetting.

3. Cryopreservation and Recovery

Cryopreservation: DMEM complete medium was refreshed 24 h before cryopreservation, so as to keep cell growth in logarithmic phase. The medium in the flask was removed under aseptic condition in a clean bench. After adherent cells were washed twice with D-hanks solution, 1 ml 0.25% trypsin was added and the flask was kept in a $CO_2$ incubator at 37° C. under 5% $CO_2$ and 95% humidity for 4~5 min. When cytoplasmic retraction and increased intercellular space of most cells were observed under microscope (even a few floating cells were observed), 4 ml DMEM complete medium was added. The single cell suspension was obtained by pipetting and cell pellet was collected by centrifuge at 1500 rpm for 10 min at room temperature. And then cells were resuspended with 1.5 ml cryopreservation solution and cell counting was performed so as to adjust the concentration of cells to $5 \times 10^6$ cells/ml. The suspension was transferred into a cell freezing tube and sealed carefully. The freezing tube was labeled with the following information: cell type, date of cryopreservation and name of the operator. Cell freezing tube was placed at −80° C. for over 12 h, and kept in liquid nitrogen on the next day.

Recovery: Cell freezing tube was taken out of liquid nitrogen and immersed in warm water at 37° C. rapidly. After cell suspension was thawed, it was transferred into a centrifuge tube and centrifuged at 1500 rpm for 10 min. The supernatant was discarded. A total volume of 5 ml DMEM complete medium was added to resuspend the pellet to single cell suspension with the cell concentration of $5 \times 10^5$ cells/ml by pipetting. Then the suspension was transferred to a culture flask and incubated in a $CO_2$ incubator at 37° C. under 5% $CO_2$ and 95% humidity.

The formulations of culture solutions of the present invention are as follows:

D-Hanks solution: NaCl 8.0 g, KCl 0.4 g, $Na_2HPO_4 \cdot 12H_2O$ 0.08 g, $KH_2PO_4$ 0.06 g, $NaHCO_3$ 0.35 g, 1% 2 ml of phenol-red were dissolved in ultra-pure water to the volume of 1000 ml. The solution was then autoclaved at 121° C. for 30 min, and stored at 4° C.

DMEM medium: Hyclone, Invitrogen (high glucose, supplemented with sodium pyruvate and L-glutamine).

DMEM complete medium: DMEM medium, 10% fetal bovine serum, penicillin 100 U/ml, streptomycin 100 µg/ml.

Cryopreservation solution (freshly prepared before use): The cryopreservation solution was composed of fetal bovine serum and dimethyl sulfoxide (DMSO) with a volume ratio of 14 to 20:1.

Example 2

Identification of the Growth and Genetic Properties of the sRCC Cell Line of from a Han Chinese of the Present Invention (RCC09HYF)

1. Morphology of RCC09HYF Cells

After successful primary culture, the cells were passaged with the routine method. The cells were able to grow in vitro and be stably passaged for a long period of time, with 120 passages in 12 months. The RCC09HYF cells of passage 12 were observed under an inverted microscope (200×): all the cells were adherent; at early stage of culture, the cellular shape was extremely irregular with lack contact of inhibition, and the cells exhibited diphasic differentiation (FIG. 1-A) and high heterogeneity (FIG. 1-B). Some cells showed the sarcomatoid structure (FIG. 1-B, denoted by blue arrow), while others showed the epithelial structure-clear cell RCC (FIG. 1-B, denoted by red arrow).

2. Growth Curve of RCC09HYF Cells

Figure 2:
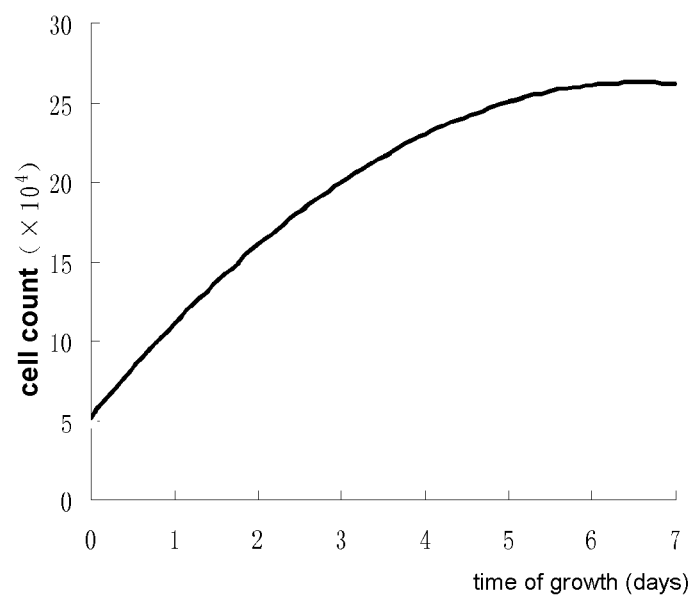
FIG. 2 shows the growth curve of RCC09HYF cells.
Figure 3:
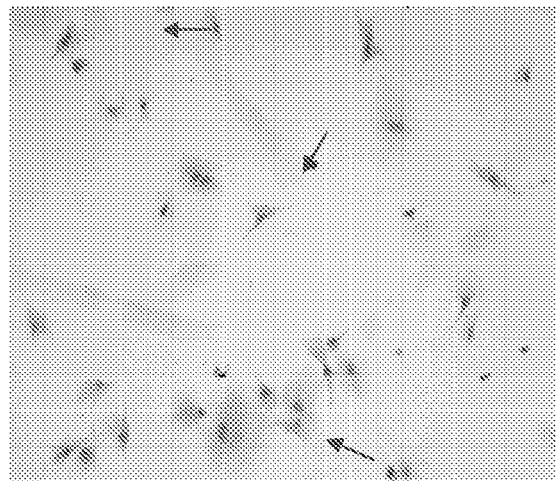
FIG. 3 shows HE staining of RCC09HYF cells. RCC09HYF cells were large in size, and exhibited clear nuclear membrane and nucleolar contour and prominent nucleoli. The cells had a little cytoplasm, high nuclear-to-cytoplasmic ratio with rich ribosomal particles and two or more nuclei in most cells. The arrow indicates the cell with two nucleus.

The total number of $5 \times 10^4$ cells suspended in 2 ml 1640 complete medium per well were seeded into 21 wells of a 24-well plate. Every other day the cells of every three wells were digested for cell counting and the mean with standard deviation were calculated to generate growth curve. As shown in FIG. 2, cells kept the logarithmic growth from 1st day to 4th day, and reached the plateau phase since 5th day with the doubling time of 18 h.

3. HE Staining of RCC09HYF Cells

RCC09HYF cells at logarithmic growth phase were harvested, washed by PBS, and fixed by 95% ethanol solution.

After washed by PBS, cells were stained by hematoxylin and eosin solution and then decolored by gradient alcohol solutions, fixed and mounted with neutralbalsam. Under the microscope, RCC09HYF cells were large in size, and exhibited clear nuclear membrane and nucleolar contour and prominent nucleoli. The cells had a little cytoplasm, high nuclear-to-cytoplasmic ratio with rich ribosomal particles and two or more nuclei in most cells. The arrow indicates the cell with two nuclei.

4. Double-Layered Soft Agarose Assay of RCC09HYF Cells (The Single Well of a 6-Well Plate was Taken as the Unit of Analysis)

Firstly, the lower layer of agarose was prepared as follows: the agorose mixture with the final concentration of 0.6% was formulated using 1.8% agarose, 2×DMEM, 100×L-glutamine, 100×mycillin and fetal bovine serum, and then solidified. After RCC09HYF cells were digested, the cells were counted and adjusted to the concentration of 5000 cells/ml. The upper layer of agarose was prepared as follows: the agarose mixture with the final concentration of 0.3% was formulated using 1.8% agarose, 2×DMEM, 100×L-glutamine, 100×mycillin and fetal bovine serum, which was then thoroughly mixed with 500 µl cell suspension and immediately poured on the lower layer of agarose. After solidification, the plate was incubated in a $CO_2$ incubator. The colony formation rate was calculated through MTT staining after 15 days. Under a microscope, 10 visual fields were randomly selected and the colony formation rate was confirmed for each field by the formula as follows: Colony formation rate=Number of the clones with more than 10 cells/Number of the seeded cells×100. After incubation of 15 days, the average of the colony formation rate of RCC09HYF was 31%.

Figure 4:
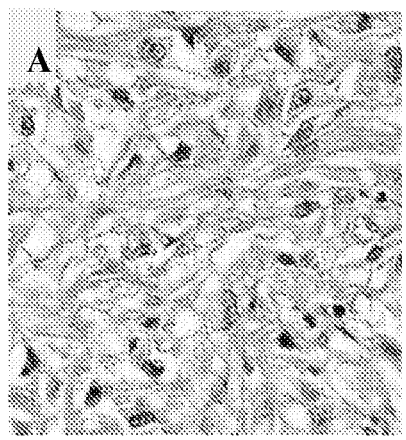
FIG. 4 shows HE staining of the original tumor tissues of RCC09HYF. Some cells exhibited sarcomatoid structure (A), while the epithelial component was mainly clear cell RCC (B).
Figure 4:
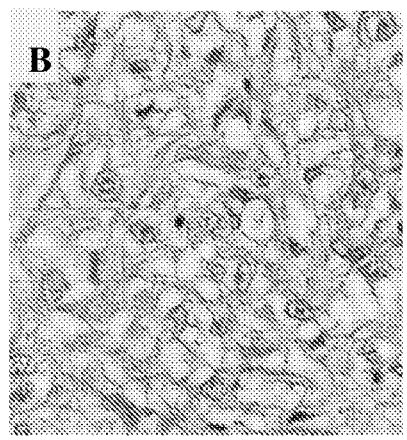
Figure 5:
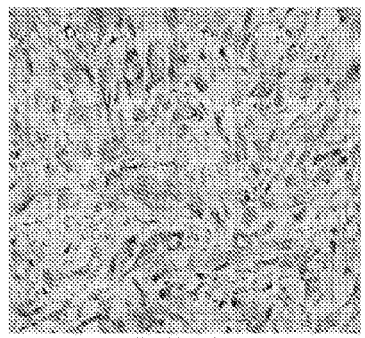
FIG. 5 shows immunohistochemical analysis of the original tumor tissues of RCC09HYF, suggesting the expression of CAM, Vimentin, CD10 and Ki67 were strongly positive.
Figure 5:
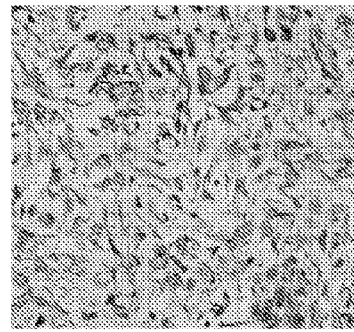
Figure 5:
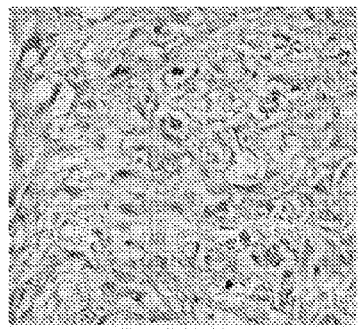
Figure 5:
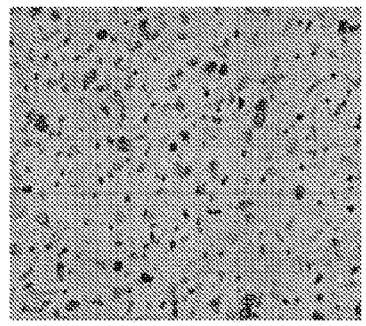
Figure 6:
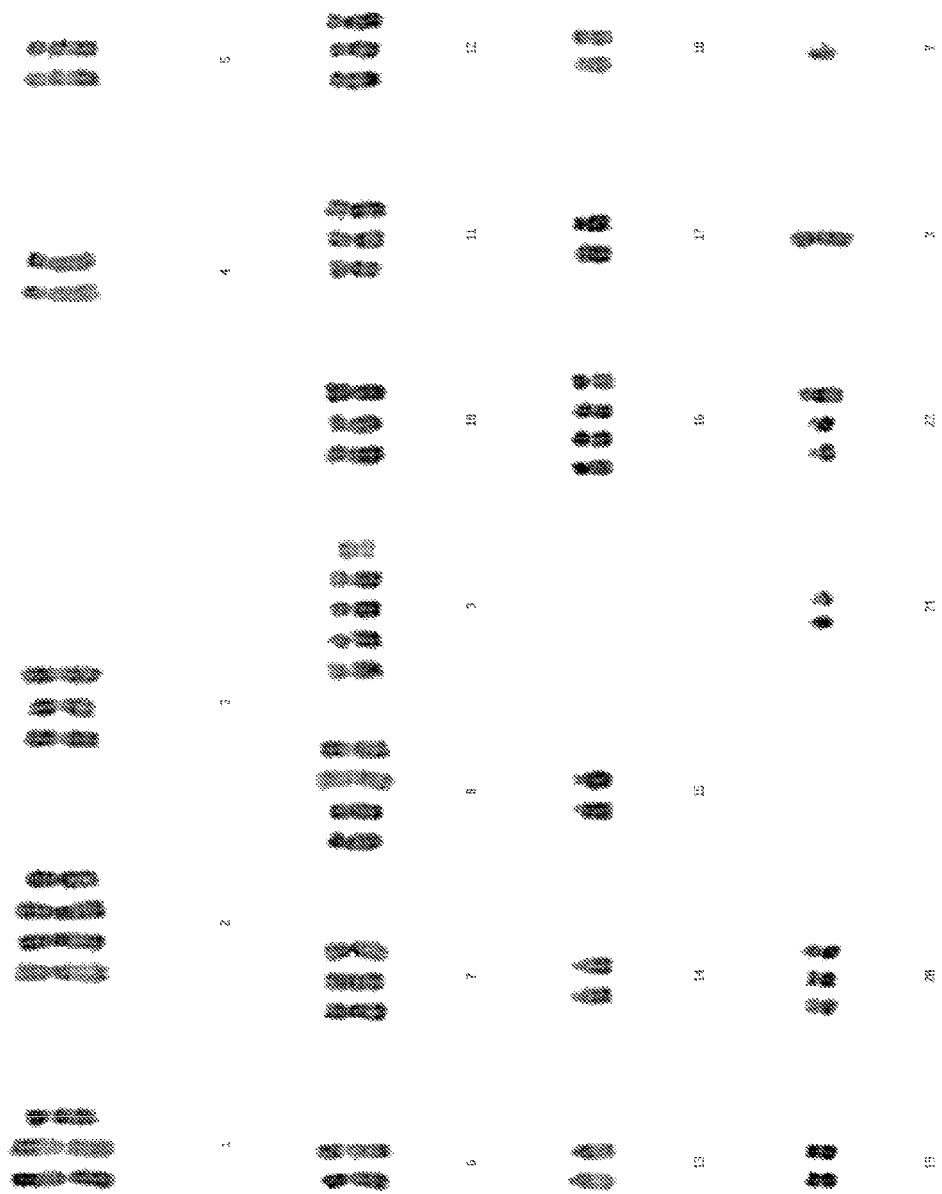
FIG. 6 shows the representative karyotype of RCC09HYF cell. As shown, RCC09HYF cell exhibited hyperdiploid, in which the number of many chromosomes was more than two.

5. HE Staining and Immunohistochemical Analysis of the Original Tumor Tissues of RCC09HYF According to the regulations of the Institutional Ethics Review Board of Second Military Medical University, the tumor tissues were obtained from the patient after informed consent. The routine paraffin sections of 4 µm thick were placed on a clean slide coated with the adhesion agent, and heated at 58° C. for 18 h. And then the conventional xylene deparaffinization was performed. HE staining under a microscope showed that some cells exhibited sarcomatoid structure (FIG. 4-A), while epithelial structure was mainly clear cell carcinoma (FIG. 4-B). For immunohistochemical analysis, the sections after deparaffinization were washed using 0.1 mol/L PBS (PH=7.4). Antigen retrieval (AR) was performed at 95° C. for 10 min, and the sections were cooled naturally and washed by PBS. Then they were incubated with the primary antibodies (Vimentin, CD10, CAM, Ki67, ABC, CACP, HMB, P53, and SMA) at 4° C. over night. After washed by PBS, the sections were dealed with by 0.3% $H_2O_2$ to inhibit the endogenous peroxidase and subsequently incubated with the secondary antibodies at 37° C. for 30 min and washed by PBS. Then, the sections were developed using 0.05% DAB+0.03% $H_2O_2$ for 8~12 min and stopped by thoroughly washed with tap water. The sections were counterstained by hematoxylin for 30 s, washed by water and blued (37° C.), followed by 0.5% hydrochloric acid alcohol differentiation and blueness and washing with water. The slides were conventionally mounted with resin. The pale brown or dark brown color with violet background was taken as positive staining. The results showed that the expression of vimentin, CD10, CAM, and Ki67 were strong positive (FIG. 5), while ABC, CACP, HMB, P53, and SMA were negative.

6. Karyotype Analysis of RCC09HYF Cells

Cells in logarithmic phase with 80%-90% confluence in monolayer culture were taken into analysis. Metakinesis was inhibited by colchicine with the final concentration of 0.04-0.1 µg/ml in the medium. The cells were further incubated in a $CO_2$ incubator for 4 h. After fixation and staining, 30 metaphase spreads were observed under a microscope. The number of chromosomes of RCC09HYF cell line ranged from 55 to 68, with the modal number of 63, indicating cases of hyperdiploid. Besides, the structure of chromosomes was analyzed by R band staining (Zheng Er, ed. Tissue Culture and Molecular and Cellular Technology. Beijing Publication House, 2001-1-1).

Table 1 and Table 2 exhibit karyotype analysis of RCC05HYF. 30 metaphase spreads were analyzed and the abnormal cases were counted. The abberation observed in more than 10 division phases were listed in Tables 1 and Table 2: Chromosome 1 had deletion, with the detection rate of 90.0%. Hyperdiploid generally existed in Chromosomes 7, 9, 10, 11, and 12, with the detection rate of 96.7%, 100%, 83.3%, 96.7%, and 100%, respectively. Meanwhile, the abnormal structures also existed in Chromosomes 9, 11 and 12, with the detection rate of 100%, 56.7%, and 63.3%, respectively. Besides, the abnormal structures, del(1) (qter→p31:) and del(2) (pter→q33:), were widespread in Chromosomes 1 and 2, with the detection rate of 93.3% (28/30) for both cases.

TABLE 1

The aberration of chromosome number of RCC09HYF cells (abnormities with more than 10 division phases)

| Numeral Aberration | | Chromosome No. | Detection rate (%, n/N) |
|---|---|---|---|
| Gain | 1~2 more than normal | 2 | 100.0 (30/30) |
| | | 3 | 83.3 (25/30) |
| | | 7 | 96.7 (29/30) |
| | | 11 | 96.7 (29/30) |
| | | 12 | 100.0 (30/30) |
| | | 16 | 40.0 (12/30) |
| | | 19 | 43.3 (13/30) |
| | | 20 | 33.3 (10/30) |
| | 2~4 more than normal | 9 | 100.0 (30/30) |
| | 1~3 more than normal | 10 | 83.3 (25/30) |
| | | 22 | 63.3 (25/30) |
| Loss | 1 less than normal | 1 | 90.0 (27/30) |
| | Deletion | 6 | 33.3 (10/30) |
| | | 21 | 70.0 (21/30) |

TABLE 2

The aberration of chromosome structure of RCC09HYF cells (abnormities with more than 10 division phases)

| Marker | Chromosome No. | Structural Aberration | Detection rate (%, n/N) |
|---|---|---|---|
| M1[1p-] | 1 | del(1) (qter→p31:) | 93.3 (28/30) |
| M2[2q-] | 2 | del(2)(pter→q33:) | 93.3 (28/30) |
| M3[i(8q)] | 8 | i(8)(qter→q10:q10→qter) | 100.0 (30/30) |
| M4[der(8)t(8; 9)] | 8 | der(8)t(8qter→q12:9p13→qter) | 100.0 (30/30) |
| M5[der(9)t(8; 9)] | 9 | del(9)t(9per→p13:8q12→pter) | 100.0 (30/30) |

TABLE 2-continued

The aberration of chromosome structure of RCC09HYF cells
(abnormities with more than 10 division phases)

| Marker | Chromosome No. | Structural Aberration | Detection rate (%, n/N) |
|---|---|---|---|
| M7[11q+] | 11 | add(11)(pter→qter::?) | 56.7 (17/30) |
| M9[12q+] | 12 | add(12)(pter→qter::?) | 63.3 (19/30) |
| M10[18p+] | 18 | add(18)(qter→pter::?) | 33.3 (10/30) |
| M11[22q+] | 22 | add(22)(pter→qter::?) | 70.0 (21/30) |

Example 3

Animal Experiments for the sRCC Cell Line of from Han Chinese of the Present Invention (RCC09HYF)

Firstly, subcutaneous tumorigenesis was performed to 4-week old nude mice using $2 \times 10^6$ cells/mouse. When tumors reached 1 cm in diameter, they were excised and transplanted into renal subcapsules to establish the orthotopic models and observed tumorigenic and metastatic potential of RCC09HYF cells. Orthotopic transplantation in the renal subcapsule was performed as follows. After mechanically minced, the tissue pieces from the subcutaneous tumor were suspended in serum-free DMEM and kept on ice for future transplantation. Nude mice of 4-week old were weighed, and anaesthetized using 1% pentobarbital sodium in an amount of 70~80 μl/10 g by intraperitoneal injection. Operation started after the mice were anaesthetic. Took mice in right lateral position, and disinfected the skins of back and belly on the left side of mice using 75% alcohol wipes. A longitudinal incision of 1~1.3 cm was made in the left renal region parallel to the spine using an ophthalmic scissor. The epidermis, subcutaneous tissue, and perirenal fascia were cut open, and the left kidney was pushed and brought out of nephridial pit by sterile swabs. The renal capsule was carefully cut by an ophthalmic scissor to create a small incision of 2~3 mm. RCC tissue pieces were put under the renal capsule and away from the incision using an ophthalmic forceps. Then the incision was covered by the perirenal fat tissue. The perirenal fascia was sutured using 6-0 silk thread under pressure, and the skin was sutured using 4-0 silk thread. The mice were then kept in cages for observation. The mice were sacrificed by cervical dislocation before dying, and tumorgenesis and metastasis were observed. It was found that RCC09HYF tumorigenesis was relatively stronger in nude mice. Three to four weeks after orthotopic transplantation, the whole abdominal cavity was full of tumor in above 50% of nude mice and dyscrasia appeared. Moreover, lung metastasis was detected in a few individuals.

The invention claimed is:

1. A method for generating a sarcomatoid renal cell carcinoma (sRCC) cell line from a Han Chinese patient comprising:
    providing primary tumor tissue from a Han Chinese sRCC patient;
    immersing said primary tumor tissue in serum-free culture medium at about 4° C. for about 30 min;
    cutting said immersed primary tumor tissue into approximately 1-3 mm³ pieces;
    washing said primary tumor tissue pieces in serum-free culture medium;
    suspending said washed primary tumor tissue pieces in complete culture medium;
    seeding said suspended primary tumor tissue pieces into a culture vessel; and
    incubating said seeded primary tumor tissue pieces for 24 h at 37° C. under 5% $CO_2$ and 95% humidity until at least some seeded primary tumor tissue pieces adhere to the culture vessel, wherein said adherent primary tumor tissue pieces are an sRCC culture.

2. The method of claim 1 wherein the serum-free culture medium is Dulbecco's Modified Eagle Medium (D-MEM).

3. The method of claim 2 wherein the D-MEM contains about 1000 U/mL of penicillin and about 3 μg/mL of amphotericin B.

4. The method of claim 1 wherein the washing of said primary tumor tissue pieces comprises:
    shaking the primary tumor tissue pieces in D-MEM for about 2-3 minutes;
    centrifuging the shaken primary tumor tissue pieces at 1500 rpm for 10 min to produce a first supernatant and a first pellet;
    discarding the first supernatant;
    resuspending the first pellet in D-MEM;
    shaking the resuspended first pellet for about 2-3 minutes;
    centrifuging the shaken first pellet at 1500 rpm for 10 min to produce a second supernatant and a second pellet; and
    discarding the second supernatant.

5. The method of claim 1 wherein the complete medium comprises D-MEM, 10% fetal bovine serum, 100 U/ml penicillin, and 100 μg/ml streptomycin.

6. The method of claim 1 further comprising:
    incubating the sRCC culture.

7. The method of claim 1 further comprising:
    incubating the sRCC culture until the culture reaches about 85% confluence; and
    passaging the cells into one or more new culture vessels.

8. The method of claim 1 wherein the primary tumor tissue comprises one or more of hemangiopericytosarcomatoid, rhabdomyosarcomatoid, osteosarcomatoid, chondrosarcomatoid and undifferentiated sarcomatoid cells.

9. A mouse model for sRCC comprising a nude mouse wherein the sRCC cell line of claim 1 is implanted in the renal capsule of said nude mouse.

10. The mouse model of claim 9 wherein the sRCC tissue is derived from RCC09HYF, deposited with the China Center for Type Culture Collection under accession number C201130.

11. An sRCC cell line produced by the method of claim 1.

12. An sRCC cell line from a Han Chinese patient, RCC09HYF, deposited with the China Center for Type Culture Collection under accession number C201130.

* * * * *